US00PP30798P2

(12) United States Plant Patent
Kobayashi

(10) Patent No.: US PP30,798 P2
(45) Date of Patent: Aug. 13, 2019

(54) **NEW GUINEA *IMPATIENS* PLANT NAMED 'DOIMSSDARE'**

(50) Latin Name: *Impatiens hawkeri*
Varietal Denomination: Doimssdare

(71) Applicant: DUMMEN GROUP B.V., De Lier (NL)

(72) Inventor: Ruth Kobayashi, Carlsbad, CA (US)

(73) Assignee: Dümmen Group B.V., De Lier (NL)

( * ) Notice: Subject to any disclaimer, the term of this patent is extended or adjusted under 35 U.S.C. 154(b) by 0 days.

(21) Appl. No.: 15/932,933

(22) Filed: May 23, 2018

(51) Int. Cl.
*A01H 5/02* (2018.01)
*A01H 6/16* (2018.01)

(52) U.S. Cl.
USPC ..... Plt./318.7

(58) Field of Classification Search
USPC ..... Plt./317, 318.1, 318.7
See application file for complete search history.

*Primary Examiner* — Susan McCormick Ewoldt
(74) *Attorney, Agent, or Firm* — C. A. Whealy

(57) ABSTRACT

A new and distinct cultivar of *Impatiens* plant named 'Doimssdare' characterized by its upright, outwardly spreading and mounding plant habit; moderately vigorous growth habit; freely branching habit; dark green-colored leaves; freely and early flowering habit; dark red-colored flowers; and good garden performance.

2 Drawing Sheets

Botanical designation: *Impatiens hawkeri.*
Cultivar denomination: 'DOIMSSDARE'.

BACKGROUND OF THE INVENTION

The present invention relates to a new and distinct cultivar of New Guinea *Impatiens* plant, botanically known as *Impatiens hawkeri* and hereinafter referred to by the name 'Doimssdare'.

The new *Impatiens* plant is a product of a planned breeding program conducted by the Inventor in Encinitas, Calif. The objective of the breeding program is to create new early and freely flowering New Guinea *Impatiens* plants with attractive flowers and good garden performance.

The new *Impatiens* plant is a naturally-occurring whole plant mutation of a proprietary selection of *Impatiens hawkeri* identified as code number NN-1168-X0000, not patented. The new *Impatiens* plant was discovered and selected by the Inventors as a single flowering plant from within a population of plants of the parent selection in a controlled greenhouse environment in Encinitas, Calif. on Jan. 12, 2015.

Asexual reproduction of the new *Impatiens* plant by terminal vegetative cuttings in a controlled greenhouse environment in Encinitas, Calif. since Apr. 24, 2015 has shown that the unique features of this new *Impatiens* plant are stable and reproduced true to type in successive generations.

SUMMARY OF THE INVENTION

Plants of the new *Impatiens* have not been observed under all possible combinations of environmental conditions and cultural practices. The phenotype may vary somewhat with variations in environmental conditions such as temperature, daylight and light intensity without, however, any variance in genotype.

The following traits have been repeatedly observed and are determined to be the unique characteristics of 'Doimssdare'. These characteristics in combination distinguish 'Doimssdare' as a new and distinct *Impatiens* plant:

1. Upright, outwardly spreading and mounding plant habit.
2. Moderately vigorous growth habit.
3. Freely branching habit.
4. Dark green-colored leaves.
5. Freely and early flowering habit.
6. Dark red-colored flowers.
7. Good garden performance.

Plants of the new *Impatiens* can be compared to plants of the mutation parent selection. Plants of the new *Impatiens* differ primarily from plants of the mutation parent selection in flower color as plants of the mutation parent selection have orange-colored flowers.

Plants of the new *Impatiens* can be compared to plants of *Impatiens hawkeri* 'Duemagdarre', disclosed in U.S. Plant Pat. No. 25,777. In side-by-side comparisons, plants of the new *Impatiens* differ primarily from plants of 'Duemagdarre' in the following characteristics:

1. Plants of the new *Impatiens* flower about two weeks earlier than plants of 'Duemagdarre'.
2. Plants of the new *Impatiens* have smaller flowers than plants of 'Duemagdarre'.

Plants of the new *Impatiens* can also be compared to plants of *Impatiens hawkeri* 'SAKIMP022', disclosed in U.S. Plant Pat. No. 23,500. In side-by-side comparisons, plants of the new *Impatiens* differ primarily from plants of 'SAKIMP022' in the following characteristics:

1. Plants of the new *Impatiens* are more upright than and not as spreading as plants of 'SAKIMP022'.
2. Plants of the new *Impatiens* and 'SAKIMP022' differ in flower color as plants of 'SAKIMP022' have cherry red-colored flowers.

BRIEF DESCRIPTION OF THE PHOTOGRAPHS

The accompanying colored photographs illustrate the overall appearance of the new *Impatiens* plant showing the colors as true as it is reasonably possible to obtain in colored reproductions of this type. Colors in the photographs may differ slightly from the color values cited in the detailed botanical description which accurately describe the colors of the new *Impatiens* plant.

The photograph on the first sheet is a side perspective view of a typical flowering plant of 'Doimssdare' grown in a container.

The photograph on the second sheet is a close-up view of a typical flowering plant of 'Doimssdare'.

DETAILED BOTANICAL DESCRIPTION

The aforementioned photographs and following observations, measurements and values describe plants grown during the winter and early spring in 10-cm containers in a polyethylene-covered greenhouse in Encinitas, Calif. and under cultural practices typical of commercial New Guinea *Impatiens* production. During the production of the plants, day temperatures averaged 25° C., night temperatures averaged 20° C. and light levels ranged from 4,000 to 4,500 lux. Plants were twelve weeks old when the photographs and description were taken. In the following description, color references are made to The Royal Horticultural Society Colour Chart, 2007 Edition, except where general terms of ordinary dictionary significance are used.

Botanical classification: *Impatiens hawkeri* 'Doimssdare'.

Parentage: Naturally-occurring whole plant mutation of a proprietary selection of *Impatiens hawkeri* identified as code number NN-1168-X0000, not patented.

Propagation:

- *Type*.—By terminal vegetative cuttings.
- *Time to initiate roots, summer and winter*.—About five to seven days at temperatures about 20° C.
- *Time to produce a rooted young plant, summer and winter*.—About three weeks at temperatures about 20° C.
- *Root description*.—Fine, fibrous; typically white in color, actual color of the roots is dependent on substrate composition, water quality, fertilizers, substrate temperature and age of roots.
- *Rooting habit*.—Freely branching; dense.

Plant description:

- *Plant and growth habit*.—Upright to outwardly spreading and mounding plant habit; freely branching habit with about eleven primary lateral branches developing per plant; moderately vigorous growth habit and moderate growth rate.
- *Plant height*.—About 20 cm.
- *Plant diameter*.—About 31 cm.

Lateral branch description:

- *Length*.—About 14 cm.
- *Diameter*.—About 8 mm.
- *Internode length*.—About 5.5 cm.
- *Strength*.—Strong.
- *Aspect*.—Initially upright to outwardly spreading.
- *Texture and luster*.—Smooth, glabrous; moderately glossy.
- *Color, developing*.—Close to 146A.
- *Color, fully developed*.—Close to 146A heavily tinged with close to 59A.

Leaf description:

- *Arrangement*.—Opposite or in whorls; simple.
- *Length*.—About 11 cm.
- *Width*.—About 4.5 cm.
- *Shape*.—Elliptic.
- *Apex*.—Apiculate to acuminate.
- *Base*.—Attenuate.
- *Margin*.—Serrulate with ciliation.
- *Texture and luster, upper and lower surfaces*.—Smooth, glabrous; leathery; moderately glossy.
- *Venation pattern*.—Pinnate; arcuate.
- *Color*.—Developing and fully expanded leaves, upper surface: Darker than 147A; venation, close to 59A. Developing and fully expanded leaves, lower surface: Close to 147B; venation, close to 59A.
- *Petiole length*.—About 2.5 cm.
- *Petiole diameter*.—About 3 mm.
- *Petiole texture and luster, upper and lower surfaces*.—Smooth, glabrous; moderately glossy.
- *Petiole color, upper and lower surfaces*.—Close to 59A.

Flower description:

- *Flower type and flowering habit*.—Single rounded and flat axillary flowers; freely flowering habit, typically about seven to nine open flowers and flower buds per lateral branch; flowers positioned above and beyond the foliar plane, flowers typically face mostly upright to outwardly.
- *Flower longevity*.—Flowers typically last about four to seven days on the plant under greenhouse conditions; petals self-cleaning, gynoecium persistent.
- *Fragrance*.—None detected.
- *Natural flowering season*.—Year-round under greenhouse conditions; in the garden, flowering from spring until fall in Germany; early flowering habit, plants typically begin flowering about twelve weeks after planting.
- *Flower buds*.—Length: About 2.5 cm. Diameter: About 1.5 cm. Shape: Ovate. Color: Close to 144A heavily tinged with close to 59A.
- *Flower diameter*.—About 7.2 cm by 7.2 cm.
- *Flower depth*.—About 3.5 cm.
- *Petals*.—Quantity and arrangement: Five per flower in a single whorl. Length: About 3.6 cm. Width: About 4.4 cm. Shape: Obcordate. Apex: Cordate; rounded. Base: Acute. Margin: Entire, occasionally with a shallow notch. Texture and luster, upper and lower surfaces: Smooth, glabrous; velvety; slightly glossy. Color: When opening and fully opened, upper surface: Close to 45B; venation, close to 45B; color becoming closer to 45A with development, When opening and fully opened, lower surface: Close to 45D; venation, close to 45D.
- *Sepals*.—Quantity and arrangement: Three in a single whorl; one modified into an elongated spur. Length: About 1 cm. Width: About 5 mm. Shape: Broadly lanceolate. Apex: Apiculate. Base: Acute. Margin: Entire. Texture and luster, upper and lower surfaces: Smooth, glabrous; moderately glossy. Color, upper and lower surfaces: Close to 59A. Spur length: About 5.5 cm. Spur diameter: At flower, about 2.75 mm; at apex, about 1 mm. Spur texture and luster: Smooth, glabrous; moderately glossy. Spur color: Close to 59A.
- *Peduncles*.—Length: About 5.75 cm. Diameter: About 4.5 mm. Angle: Upright to outwardly. Strength: Moderately strong; flexible. Texture and luster: Smooth, glabrous; moderately glossy. Color: Close to 59A.

*Reproductive organs*.—Stamens: Quantity: Five fused at anthers; filaments free. Anther length: About 5 mm. Anther shape: Oval. Anther color: Close to 11A and 45B. Pollen amount: Scarce. Pollen color: Close to 11D. Pistils: Quantity per flower: One. Pistil length: About 5.75 mm. Stigma shape: Crested. Stigma color: Close to 157A. Style color: Close to 144A. Ovary color: Close to 144A.

*Seeds and fruits*.—To date, seed and fruit production has not been observed on plants of the new *Impatiens*.

Disease & pest resistance: To date, plants of the new *Impatiens* have not been observed to be resistant to pathogens and pests common to *Impatiens* plants.

Garden performance: Plants of the new *Impatiens* have been observed to have good garden performance and tolerate temperatures ranging from about 5° C. to about 40° C.

It is claimed:

1. A new and distinct *Impatiens* plant named 'Doimssdare' as illustrated and described.

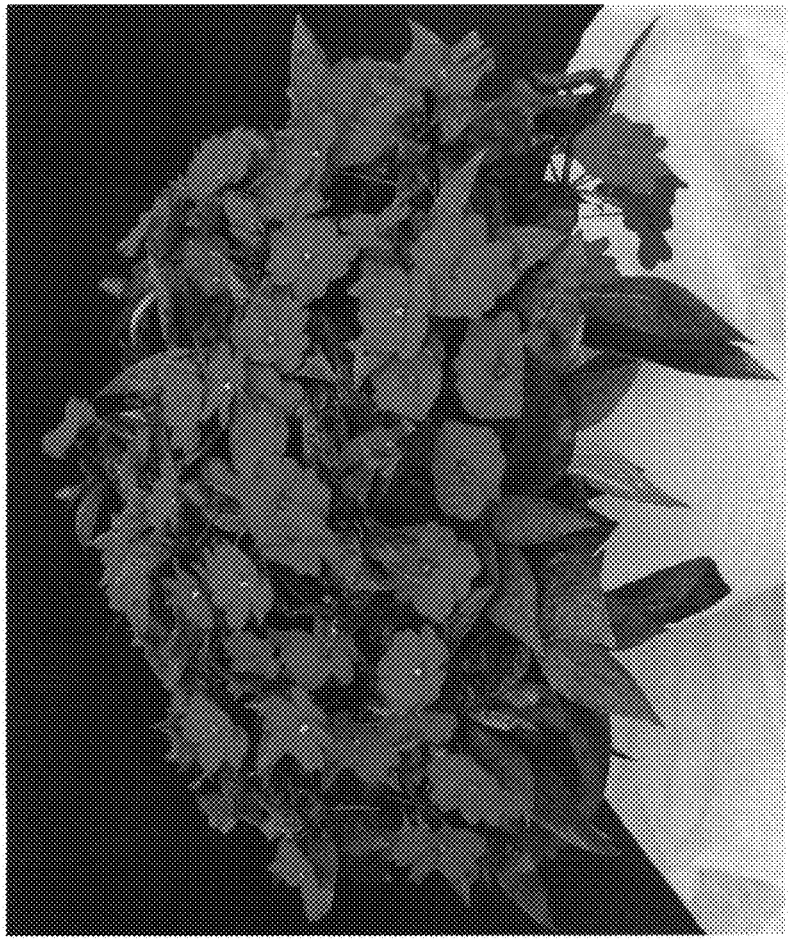

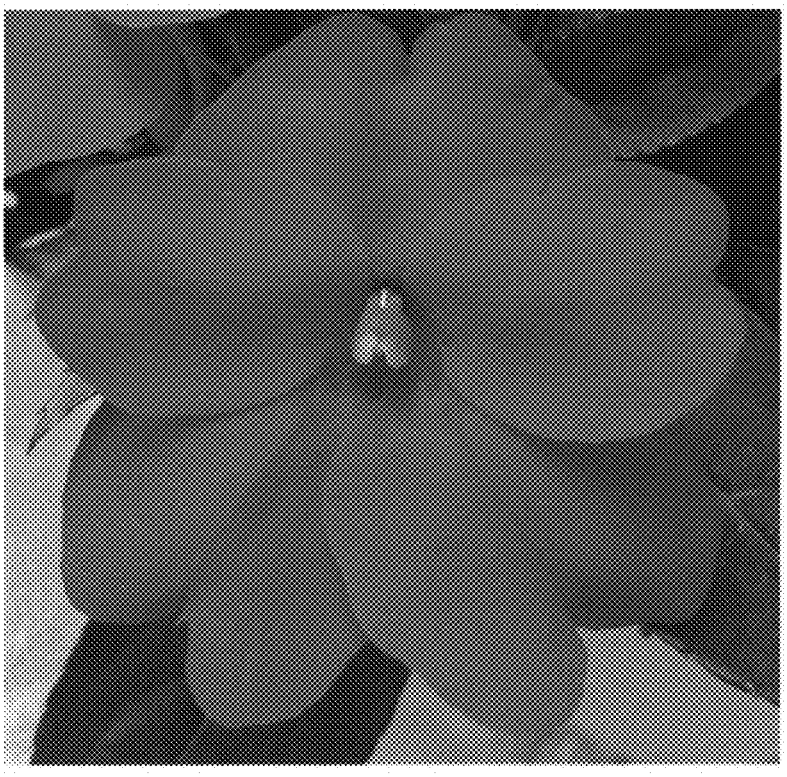

* * * * *